United States Patent

Teetz et al.

Patent Number: 4,797,471
Date of Patent: Jan. 10, 1989

[54] PEPTIDE DERIVATIVES HAVING AN INHIBITORY ACTION ON HYDROXYLATING ENZYMES, A PROCESS FOR THEIR PREPARATION, AGENTS CONTAINING THEM, AND THEIR USE

[75] Inventors: Volker Teetz, Hofheim am Taunus; Stephan Henke, Bad Soden am Taunus; Dietrich Brocks, Wiesbaden; Hartmut Hanauske-Abel, Dexheim; Volkmar Günzler, Marburg-Cappel, all of Fed. Rep. of Germany

[73] Assignee: Hoechst Aktiengesellschaft, Frankfurt am Main, Fed. Rep. of Germany

[21] Appl. No.: 941,066

[22] Filed: Dec. 12, 1986

[30] Foreign Application Priority Data

Dec. 14, 1985 [DE] Fed. Rep. of Germany ....... 3544338

[51] Int. Cl.$^4$ ........................ H61K 37/43; C07K 5/08
[52] U.S. Cl. ........................................ 514/18; 530/331
[58] Field of Search ........................... 514/18; 530/331

[56] References Cited

U.S. PATENT DOCUMENTS 4,457,936 7/1984 Draeger et al.

OTHER PUBLICATIONS

Computer printout.

Primary Examiner—Delbert R. Phillips
Attorney, Agent, or Firm—Finnegan, Henderson, Farabow, Garrett & Dunner

[57] ABSTRACT

The invention relates to peptide derivatives of the formula

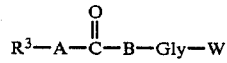

in which

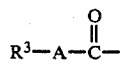

represents an acyl radical, B represents the radical of a dipeptide composed of a $N^\omega$-acylated basic α-amino acid and another α-amino acid, and W represents hydroxyl or optionally substituted amino, to a process for their preparation, to agents containing them, and to their use.

11 Claims, No Drawings

PEPTIDE DERIVATIVES HAVING AN INHIBITORY ACTION ON HYDROXYLATING ENZYMES, A PROCESS FOR THEIR PREPARATION, AGENTS CONTAINING THEM, AND THEIR USE

U.S. Pat. No. 4,457,936 discloses hydroxyphenyl-thiazole-, -thiazoline- and -thiazolidine-carboxylic acids and their use as inhibitors of proline hydroxylase and lysine hydroxylase.

It has been found that certain peptide derivatives of α, ω-diaminoalkanecarboxylic acids having hydroxy-substituted phenylacyl in the $N^\omega$ position are highly active inhibitors of hydroxylating enzymes.

Hence the invention relates to compounds of the formula I

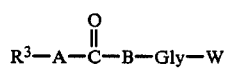

in which
R$^3$ denotes (C$_1$–C$_8$)-alkyl which is optionally monosubstituted by carboxyl, amino, hydroxyl or (C$_1$–C$_4$)-alkoxy; (C$_3$–C$_8$)-cycloalkyl; (C$_3$–C$_8$)-cycloalkyl-(C$_1$–C$_5$)-alkyl; (C$_6$–C$_{10}$)-aryl or (C$_6$–C$_{10}$)-aryl-(C$_1$–C$_5$)-alkyl, both of which can optionally be substituted in the aryl moiety by one or two, identical or different, radicals from the series comprising carboxyl, amino, hydroxyl, (C$_1$–C$_4$)-alkoxy or halogen; (C$_3$–C$_9$)-heteroaryl or (C$_3$–C$_6$)-heteroaryl-(C$_1$–C$_5$)-alkyl;
A represents —O—, —NH— or a direct bond;
B denotes a radical of the formula IIIa or IIIb;

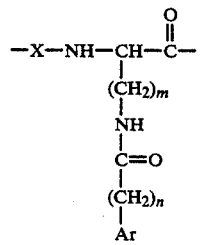

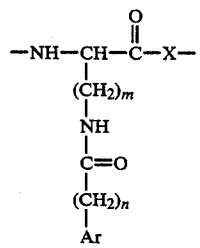

in which
X represents a radical of proline or 4-thiaproline or a radical of the formula IV

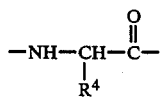

in which
R$^4$ denotes hydrogen or (C$_1$–C$_4$)-alkyl which is optionally monosubstituted by hydroxyl, carboxyl, carbamoyl, methylthio, phenyl, 4-hydroxyphenyl, 4-imidazolyl or 3-indolyl;
m represents 2, 3 or 4,
n represents 0 or 1, and
Ar represents mono-, di- or trihydroxyphenyl, and
W denotes hydroxyl or a radical of the formula V

in which
R$^1$ denotes hydrogen, (C$_1$–C$_6$)-alkyl or (C$_3$–C$_6$)-cycloalkyl, and
R$^2$ denotes hydrogen, (C$_1$–C$_6$)-alkyl or (C$_3$–C$_6$)-cycloalkyl, or
R$^1$ and R$^2$ together represent —[CH$_2$]$_4$— or —[CH$_2$]$_5$—, it being possible for one [CH$_2$] group to be replaced by —O— or —S—,
and to their physiologically tolerated salts.

Alkyl can be straight-chain or branched. Cyclo-alkyl can carry, such as, for example, in 4-methylcyclohexyl, (one) alkyl side chain(s).

Aryl is understood to be, for example, phenyl or naphthyl, but preferably phenyl.

A heteroaryl radical within the meaning of the present invention is the radical of a monocyclic or bicyclic (C$_3$–C$_9$)-heteroaromatic which contains in the ring system one or two N atoms and/or one S or one O atom. On the term "heteroaromatic" see Garratt, Vollhardt, Aromatizität (Aromaticity), Stuttgart 1973, pages 131–153. Examples of suitable heteroaryl radicals are the radicals of thiophene, furan, benzothiophene, benzofuran, pyrrole, imidazole, pyrazole, pyridine, pyrazine, pyrimidine, pyridazine, indole, quinoline, isoquinoline, oxazole, isoxazole, thiazole and isothiazole.

Unless otherwise indicated, centers of chirality can exist both in the R and in the S configuration.

R$^3$ preferably represents optionally substituted (C$_1$–C$_8$)-alkyl, cyclopropyl, cyclobutyl, cyclopentyl, cyclohexyl, cyclopropylmethyl, cyclobutylmethyl, cyclopentylmethyl, cyclohexylmethyl, optionally substituted phenyl, optionally substituted benzyl, optionally substituted phenethyl, a heteroaryl radical from the series comprising 2-, 3- or 4-pyridyl, 2- or 3-pyrrolyl, 2- or 3-furyl, 2- or 3-thienyl, 4-imidazolyl or 1-, 3- or 4-isoquinolyl or such a heteroaryl radical which is bonded via —CH$_2$— or —CH$_2$—CH$_2$—, and in particular represents (C$_1$–C$_8$)-alkyl (for example methyl or ethyl), (C$_1$–C$_8$)-alkyl which is monosubstituted by amino, hydroxyl, carboxyl, methoxy or ethoxy, or represents cyclopentyl, cyclohexyl, phenyl or mono- or dihalogenophenyl.

B is the radical of a dipeptide which is composed of a basic amino acid which has the R or S configuration, such as α,γ-diaminobutyric acid, ornithine or lysine, and which is linked via a peptide bond via either the α-amino or the carboxyl group to the radical X, and whose ω-amino group is connected via an amide bond to substituted benzoyl or phenylacetyl, and which is represented by the above-mentioned part-formulae IIIa and IIIb.

X preferably denotes a radical of proline or 4-thiaproline or a radical of the formula IV in which R$^4$ represents hydrogen, methyl, hydroxymethyl, 1-hydroxyethyl, isopropyl, isobutyl, sec.-butyl, carboxymethyl, 2-carboxyethyl, carbamoylmethyl, 2-carbamoylethyl, 2-methylthioethyl, phenylmethyl, (4-hydroxyphenyl)-methyl, 4-imidazolylmethyl or 3-indolylmethyl, and is preferably in the S configuration. X denotes, in particular, the radical of 4-thiaproline or the radical of a naturally occurring α-amino acid (see Schröder, Lübke, The Peptides, Volume I, New York 1965, pages 137–270), such as Gly, Pro, His, Glu or Leu.

The radical Ar preferably carries in the 2- and/or in the 3-position a hydroxyl group. Examples of suitable radicals Ar are 2-hydroxyphenyl, 3-hydroxyphenyl, 4-hydroxyphenyl, 2,3-dihydroxyphenyl, 3,4-dihydroxyphenyl or 3,4,5-trihydroxyphenyl.

The C-terminal radical W preferably has the meanings hydroxyl, amino, ($C_1$–$C_6$)-alkylamino, cyclohexylamino, dimethylamino, diethylamino, ethylmethylamino, 1-piperidyl or 1-pyrrolidyl.

Particularly suitable salts are alkali metal and alkaline earth metal salts, salts with physiologically tolerated amines and salts with inorganic or organic acids such as, for example, hydrochloric acid, hydro-bromic acid, sulfuric acid, maleic acid or fumaric acid.

The invention also relates to a process for the preparation of compounds of the formula I, which comprises synthesis of the compounds in a manner known per se by condensation of the fragments, where appropriate elimination of protective groups which have been introduced temporarily, and conversion of the resulting compounds of the formula I where appropriate into their physiologically tolerated salts. Fragments within the above meaning are understood to be amino acids or their derivatives and segments containing several amino acids (such as, for example, $R^3$—A—CO—B—OH).

The condensation can be effected by, for example, condensation of a fragment of a compound of the formula I with a terminal carboxyl group or a reactive acid derivative with another fragment which contains a free amino group, it being possible for any other functional groups which are present to be protected where appropriate, with the formation of an amide bond. Methods suitable for the preparation of an amide bond are described in Houben-Weyl, Methoden der Organischen Chemie (Methods of organic chemistry), Volume 15/2. The following methods are preferably employed: The active ester method with N-hydroxysuccinimide as ester component, coupling with DCC/HOBt, and coupling with propanephosphonic anhydride.

Protective groups suitable for the temporary protection of other functional groups are those which can be eliminated under conditions under which the radicals Ar—[$CH_2$]$_n$—CO— and $R^3$—A—CO— remain on the molecule. Protective groups in peptide synthesis are described in, for example, Kontakte Merck 3/79, pages 14–22 and 1/80, pages 23–35.

Since the compounds of the formula I, according to the invention, inhibit enzymatically catalyzed hydroxylation reactions, they are suitable for preventing the maturation of proteins which do not become functionally active until in the hydroxylated form, and they can thus be used as fibrosuppressive, immunosuppressive or cytostatic agents. It is characteristic of various proteins, such as, for example, of the collagens or Clq, that, in the functionally active form, they contain amino acids which undergo post-translational hydroxylation. If this hydroxylation is suppressed by inhibition of the hydroxylases which catalyse this reaction, such as prolyl 4-hydroxylase, prolyl 3-hydroxylase, lysyl hydroxylase or deoxyhypusine hydroxylase, so that these proteins are now unable to undertake their physiological function.

The inhibitory action of the substances according to the invention, for example on collagen biosynthesis, can be tested in an enzyme test in analogy to the method of B. Peterkovsky and R. DiBlasio, Anal. Biochem. 66, 279–286 (1975). This entails enzymatic hydroxylation of underhydroxylated collagen in the presence of IronII) ions, α-ketoglutarate and ascorbate. The enzymes which can be used are prolyl 4-hydroxylase, prolyl 3-hydroxylase or lysl hydroxylase in a cell-free test medium. The inhibitory action can also be measured in cell or tissue culture and is reported as 50% inhibition of the enzyme reaction ($IC_{50}$).

Table 1 lists the $IC_{50}$ values of some of the compounds according to the invention.

TABLE 1

| Compound | Proline hydroxylase $IC_{50}$ ($10^{-6}$ mol/l) | Lysine hydroxylase $IC_{50}$ ($10^{-6}$ mol/l) |
|---|---|---|
| Ac—Orn(2,3-Dihydroxybenzoyl)-Pro—Gly—OH | 38 | 7 |
| Ac—Orn(3,4-Dihydroxybenzoyl)-Pro—Gly—OH | 72 | 7 |
| Ac—Orn(3,4,5-Trihydroxybenzoyl)-Pro—Gly—OH | 29 | 8 |
| Ac—Orn(3,4-Dihydroxyphenylacetyl)-Pro—Gly—OH | 140 | 37 |
| Ac—Pro—Orn(3,4-Dihydroxybenzoyl)-Gly—OH | 50 | 39 |
| Ac—Pro—Orn(3,4,5-Trihydroxybenzoyl)-Gly—OH | 17 | 26 |
| Ac—Pro—Orn(3,4-Dihydroxyphenylacetyl)-Gly—OH | 155 | 70 |

Hence the invention further relates to the use of compounds of the formula I for the inhibition of hydroxylating enzymes, to the use of these compounds as fibrosuppressive, immunosuppressive or cytostatic agents and to phramaceutical agnets containing an effective amount of these compounds and a physiologically acceptable vehicle. Administration can be intranasal, intravenous, subcutaneous or oral. The dosage of the active compound depends on the species of warm-blooded animal, the body weight, age and mode of administration.

The pharamaceutical products of the present invention are prepared in dissolving, mixing, granulating or tablet-coating processes which are known per se.

For a form for oral administration, the active compounds are mixed with the additives customary for this purpose, such as vehicles, stabilizers or inert diluents, and converted by customary methods into a suitable form for administration, such as tablets, coated tablets, hard gelatin capsules, aqueous, alcoholic or oily suspensions, or aqueous, alcoholic or oily solutions. Examples of suitable inert vehicles are gum arabic, magnesium carbonate, potassium phosphate, lactose, glucose or starch, in particular corn starch. This preparation can be effected both as dry and as wet granules. Examples of suitable oily vehicles or solvents are vegetable or animal oils, such as sunflower oil or fish-liver oil.

For subcutaneous or intravenous administration, the active compounds or their physiologically tolerated salts are converted into a solution, suspension or emulsion, if desired with the substances customary for this purpose, such as solubilizers or other auxiliaries. Examples of those suitable for this purpose are: water, propanediol or glycerol, as well as sugar solutions such as glucose or mannitol solutions, or a mixture of the said solvents.

The examples which follow serve to illustrate the present invention without intending to restrict it to them.

| List of abbreviations used: | |
|---|---|
| AA | amino acid analysis |
| Ac | acetyl |
| Boc | tert.-butoxycarbonyl |
| TLC | thin-layer chromatography |
| DCC | dicyclohexylcarbodiimide |
| DCU | dicyclohexylurea |
| DMF | dimethylformamide |
| DMSO | dimethyl sulfoxide |
| EA | ethyl acetate |
| FAB | fast atom bombardment |
| Fmoc | 9-fluorenylmethyloxycarbonyl |
| HOBt | 1-hydroxybenzotriazole |
| M | molecular peak |
| MeOH | methanol |
| MS | mass spectrum |
| NEM | N—ethylmorpholine |
| M.p. | melting point |
| THF | tetrahydrofuran |
| Z | benzyloxycarbonyl |

The other abbreviations used for amino acids and protective groups correspond to the letter code customary in peptide chemistry, as is described in, for example, Europ. J. Biochem. 138, 9–37 (1984). Unless expressly indicated otherwise, the amino acids are always of the L configuration.

| Mobile phase systems for chromatography: | |
|---|---|
| (1) CHCl$_3$/MeOH | 9:1 |
| (2) CHCl$_3$/MeOH | 8:3 |
| (3) CHCl$_3$/MeOH/CH$_3$COOH/H$_2$O | 20:15:2:2 |
| (4) CHCl$_3$/MeOH/CH$_3$COOH | 50:10:5 |

EXAMPLE 1

Ac-Orn(2,3-dihydroxybenzoyl)-Pro-Gly-OH 500 mg of Ac-Orn-Pro-Gly-OBzl, 314 mg of 2,3-dibenzyloxybenzoic acid, 127 mg of HOBt and 0.12 ml of NEM are dissolved in 20 ml of DMF. After addition of 194 mg of DCC the reaction is allowed to take place at room temperature for 18 hours. The solvent is removed by evaporation in vacuo, and the residue is dissolved in EA, and DCU is filtered off. Concentration in vacuo and chromatography of the residue on silica gel (system 1) provides 600 mg of Ac-Orn (2,3-dibenzyloxybenzoyl)-Pro-Gly-Obzl as a colorless oil, which is immediately subjected to the further sequence of reactions. For this purpose, 600 mg of the product are dissolved in 5 ml of methanol, and, after addition of Pd/C, hydrogenated at room temperature. After two hours, the catalyst is removed by filtration, and the filtrate is concentrated in vacuo and chromatographed on silica gel (system 3).

The residue comprises 164 mg of Ac-Orn(2,3-dihydroxybenzoyl)-Pro-Gly-OH. Rf (system 3)=0.5; MS (FAB): 465 (M+1).

The starting material is prepared by the following procedures:

(a) Ac-Orn-Pro-Gly-OBzl 2.0 g of Ac-Orn(Boc)-Pro-Gly-OBzl are dissolved in 5 ml of trifluoroacetic acid, and the solution is stirred at room temperature for 1 hour. After evaporation under high vacuum, 2.1 g of the trifluoroacetate of Ac-Orn-Pro-Gly-OBzl remain. R$_f$(system 2)=0.3; MS (FAB): 419 (M+1).

(b) Ac-Orn(Boc)-Pro-Gly-OBzl 6.4 g of H-Pro-Gly-OBzl, 4.6 g of Ac-Orn(Boc)-OH, 3.0 ml of NEM and 3.1 g of HOBt are dissolved in 30 ml of EA and then 4.8 g of DCC in 10 ml of EA are added. After the mixture has been stirred at room temperature for 24 hours, it is filtered and the filtrate is evaporated. Chromatography of the residue on silica gel (system 1) results in 4.7 g (yield: 41%) of the desired compound being isolated as a colorless powder. R$_f$(system 1)=0.3; MS (FAB): 519 (M+1).

(c) H-Pro-Gly-OBzl 5.0 g of Boc-Pro-OH, 7.4 g of H-Gly-OBzl, 3.0 ml of NEM and 3.1 g of HOBt are dissolved in 50 ml of EA with the addition of 5 ml of DMF. 4.8 g of DCC are added, and the mixture is left to stir at room temperature for 48 hours. After concentration in vacuo, the residue is dissolved in 50 ml of EA, and the solution is extracted by shaking twice with 30 ml of aqueous citric acid solution and twice with saturated aqueous sodium bicarbonate solution, and the organic phase is dried over sodium sulfate, filtered and evaporated. The residue is dissolved in 10 ml of trifluoroacetic acid, reaction is allowed to take place at room temperature for 1 hour, and the mixture is concentrated in vacuo. The residue crystallizes from EA/pentane.

6.6 g (yield: 61%) of H-Pro-Gly-OBzl.trifluoroacetate are obtained. MS (FAB): 263 (M+1); Rf (system 4)=0.29.

(d) Ac-Orn(Boc)-OH 9.3 g of H-Orn(Boc)-OH, 5.0 g of the N-hydroxysuccinimide ester of acetic acid and 4.1 ml of NEM in 50 ml of DMF and 10 ml of H$_2$O are allowed to react at room temperature for 3 days. The solvent is evaporated off in vacuo, and the residue is chromatographed on silica gel (system 4). 9.6 g of Ac-Orn(Boc)-OH (yield: 88%) readily crystallize from EA/diethyl ether. MS (FAB): 275 (M+1).

(e) 2,3-dibenzyloxybenzoic acid 19.8 g of 2,3-dibenzyloxybenzaldehyde are dissolved in 100 ml of acetone. While stirring vigorously and heating at 40° C., a solution of 4.0 g of KMnO$_4$ in 90 ml of H$_2$O is added within 45 min, the precipitated benzaldehyde being redissolved by the addition of a total of 150 ml of acetone. Once addition of the KMnO$_4$ solution is complete, the mixture is boiled under reflux for one hour. The hot solution is then filtered, and the precipitate is washed with hot water. The carboxylic acid crystallizes out in fine white needles on acidification of the cold aqueous solution with dilute HCl. 18.0 g of the desired compound are obtained (92% yield). MS: 334 (M+); M.p.: 185°–187° C.

(f) 2,3-dibenzyloxybenzaldehyde 13.8 g of 2,3-dihydroxybenzaldehyde, 30.4 g of benzyl chloride and 17.3 g of powdered anhydrous potassium carbonate in 160 ml of anhydrous ethanol are boiled under reflux with exclusion of moisture for 6 hours. The reaction solution is filtered, washing with ethanol, and the filtrate is evaporated in vacuo. On digestion of the residue with diisopropyl ether the known desired compound crystallizes and as white needles (M.p. 89°–91° C.).

In analogy to the procedure described in Example 1, the compounds of Examples 2–18 are prepared from Ac-Orn-OH, Ac-Lys-OH or AcDab-OH by reaction with H-Pro-Gly-OBzl or H-His-Gly-OBzl and the appropriate benzoic acid or phenylacetic acid derivatives.

| Example No. | Compound |
|---|---|
| 2 | Ac—Orn(2-Hydroxybenzoyl)-Pro—Gly—OH |
| 3 | Ac—Orn(3-Hydroxybenzoyl)-Pro—Gly—OH |
| 4 | Ac—Orn(3,4-Dihydroxybenzoyl)-Pro—Gly—OH |
| 5 | Ac—Orn(3,4,5-Trihydroxybenzoyl)-Pro—Gly—OH |
| 6 | Ac—Orn(2,3-Dihydroxyphenylacetyl)-Pro—Gly—OH |
| 7 | Ac—Orn(3,4-Dihydroxyphenylacetyl)-Pro—Gly—OH |
| 8 | Ac—Orn(2,3-Dihydroxybenzoyl)-His—Gly—OH |
| 9 | Ac—Orn(3,4-Dihydroxybenzoyl)-His—Gly—OH |
| 10 | Ac—Orn(3,4-Dihydroxyphenylacetyl)-His—Gly—OH |
| 11 | Ac—Lys(3,4-Dihydroxybenzoyl)-Pro—Gly—OH |
| 12 | Ac—Lys(3,4-Dihydroxyphenylacetyl)-Pro—Gly—OH |
| 13 | Ac—Lys(3,4-Dihydroxybenzoyl)-His—Gly—OH |
| 14 | Ac—Lys(3,4-Dihydroxyphenylacetyl)-His—Gly—OH |
| 15 | Ac—Dab(3,4-Dihydroxybenzoyl)-Pro—Gly—OH |
| 16 | Ac—Dab(3,4-Dihydroxyphenylacetyl)-Pro—Gly—OH |
| 17 | Ac—Dab(3,4-Dihydroxybenzoyl)-His—Gly—OH |
| 18 | Ac—Dab(3,4-Dihydroxyphenylacetyl)-His—Gly—OH |

A variety of analytical and spectroscopic methods was used to confirm the structures of the peptides which had been prepared thus.

Some results are compiled in Table 2.

TABLE 2

| Example No. | MS (FAB) | TLC ($R_f$) | $^1$H—NMR (a) | Others |
|---|---|---|---|---|
| 2 | 449 (M + 1) | 0.60 (Syst. 2) | + | |
| 3 | 449 (M + 1) | 0.58 (Syst. 2) | + | AA |
| 4 | 465 (M + 1) | 0.48 (Syst. 2) | + | |
| 5 | 481 (M + 1) | 0.50 (Syst. 3) | + | |
| 6 | 479 (M + 1) | 0.55 (Syst. 2) | + | |
| 7 | 479 (M + 1) | 0.69 (Syst. 3) | + | |
| 8 | 505 (M + 1) | 0.26 (Syst. 2) | + | AA |
| 9 | 505 (M + 1) | 0.45 (Syst. 2) | + | C,H,N-Analysis |
| 10 | 519 (M + 1) | 0.35 (Syst. 2) | + | C,H,N-Analysis |
| 11 | 479 (M + 1) | 0.50 (Syst. 2) | + | |
| 12 | 493 (M + 1) | 0.50 (Syst. 2) | + | |
| 13 | 519 (M + 1) | 0.32 (Syst. 2) | + | AA |
| 14 | 533 (M + 1) | 0.35 (Syst. 2) | + | |
| 15 | 451 (M + 1) | 0.38 (Syst. 2) | + | |
| 16 | 465 (M + 1) | 0.40 (Syst. 2) | + | |
| 17 | 491 (M + 1) | 0.18 (Syst. 2) | + | |
| 18 | 505 (M + 1) | 0.25 (Syst. 2) | + | |

(a) measured at 60 or 270 MHz;
"+" means: consistent with the indicated structure.

EXAMPLE 19

Ac-Pro-Orn(3,4-dihydroxybenzoyl)-Bly-OH 0.33 g of 3,4-dibenzyloxybenzoic acid, 0.14 g of HOBt and 0.45 g of Ac-Pro-Orn-Gly-OBzl are dissolved in 5 ml of DMF. The solution is then cooled to −10° C., and 0.23 g of DCC in 1 ml of DMF and 0.13 ml of NEM is added. The reaction mixture is maintained at −10° C. for 1 hour and is then stirred at room temperature for 24 hours. After the dicyclohexylurea has been removed by filtration, the filtrate is evaporated in vacuo, and the residue is chromatographed on silica gel (system 1). 0.2 g (yield: 31%) of Ac-Pro-Orn(3,4-dibenzyloxybenzoyl)-Gly-OBzl is obtained as an amorphous solid which is immediately processed further. For this process, the product is dissolved in 10 ml of methanol, and a little Pd/C is added. H$_2$ is passed in at room temperature until hydrogenolytic cleavage is complete (checked by TLC), then the mixture is filtered and the solvent is removed by evaporation in vacuo. 150 mg of the desired compound remain. R$_f$ (system 3)=0.36; MS(FAB): 465 (M+1).

The starting material is prepared by the following procedures:

(a) Ac-Pro-Orn-Gly-OBzl 1.0 g of Ac-Pro-Orn(Boc)-Gly-OBzl is dissolved in 5 ml of trifluoroacetic acid, and the soluion is stirred at room temperature for 1 hour. 1.0 g of the trifluoroacetate of Ac-Pro-Orn-Gly-OBzl remains after evaporation under high vacuum. Rf (system 2)=0.6; MS (FAB): 419 (M+1).

(b) Ac-Pro-Orn(Boc)-Gly-OBzl 5.6 g of Ac-Pro-Orn(Boc)-OH, 5.0 g of the tosylate of H-Gly-OBzl and 2.0 g of HOBt are dissolved in 50 ml of DMF, cooled to 0° C., and 1.9 ml of NEM and 3.4 g of DCC in 5 ml of DMF are added. The mixture is stirred at 0° C. for one hour, and at room temperature overnight. After the urea has been removed by filtration, the solvent is removed by evaporation in vacuo, and the residue is chromatographed on silica gel (system 4). 6.1 g (yield: 79%) of Ac-Pro-Orn(Boc)-Gly-OBzl remain as an oil. Rf (system 4)=0.75; MS (FAB): 519 (M+1).

(c) Ac-Pro-Orn(Boc)-OH 5.5 g of H-Orn(Boc)-OH and 6.0 g of Ac-Pro-OSU are dissolved in 50 ml of DMF and, after addition of 3 ml of NEM, the mixture is stirred at room temperature for 24 hours. After the solvent has been removed by distillation in vacuo, the residue is taken up in 30 ml of nbutanol, and the solution is washed twice with saturated aqueous potassium bisulfate solution and then with saturated aqueous sodium chloride solution. The solution is concentrated in vacuo, and Ac-Pro-Orn(Boc)-OH is precipitated by digestion with diethyl ether. R$_f$(system 3)=0.24; MS (FAB): 372 (M+1).

(d) Ac-Pro-OSU

A solution of 39.3 g of Ac-Pro-OH and 28.7 g of N-hydroxysuccinimide in 200 ml of dioxane is cooled to −5° C., and a previously cooled solution of 51.6 g of DCC in 100 ml of dioxane is added. The mixture is stirred at 0° C. for 1 hour and at room temperature for a further hour, and then the precipitated DCU is filtered off and thoroughly washed twice with 50 ml of dioxane. After the solvent has been removed in vacuo, the residue is taken up in 30 ml of isopropanol, and the product is precipitated overnight by addition of petroleum ether. 33.0 g (yield: 50%) of microcrystalline Ac-Pro-OSU are obtained.

MS (FAB): 255 (M+1); M.p. 100°–105° C.

In analogy to the procedure described in Example 19, the compounds of Examples 20–43 are prepared from Ac-Pro-OH, Ac-Gly-OH, Ac-Glu-OH or Ac-His-OH by reaction with ornithine, α,β-diaminobutyric acid or lysine, and glycine and the appropriate benzoic acid or phenylacetic acid derivatives.

| Example No. | Compound |
|---|---|
| 20 | Ac—Pro—Orn(2-Hydroxybenzoyl)-Gly—OH |
| 21 | Ac—Pro—Orn(3-Hydroxybenzoyl)-Gly—OH |
| 22 | Ac—Pro—Orn(2,3-Dihydroxybenzoyl)-Gly—OH |
| 23 | Ac—Pro—Orn(3,4,5-Trihydroxybenzoyl)-Gly—OH |
| 24 | Ac—Pro—Orn(2,3-Dihydroxyphenylacetyl)-Gly—OH |
| 25 | Ac—Pro—Orn(3,4-Dihydroxyphenylacetyl)-Gly—OH |
| 26 | Ac—Pro—Dab(3,4-Dihydroxybenzoyl)-Gly—OH |
| 27 | Ac—Pro—Dab(3,4-Dihydroxyphenylacetyl)-Gly—OH |
| 28 | Ac—Pro—Lys(3,4-Dihydroxybenzoyl)-Gly—OH |
| 29 | Ac—Pro—Lys(3,4-Dihydroxyphenylacetyl)-Gly—OH |
| 30 | Ac—Gly—Orn(3,4-Dihydroxybenzoyl)-Gly—OH |
| 31 | Ac—Gly—Orn(3,4-Dihydroxyphenylacetyl)-Gly—OH |
| 32 | Ac—Gly—Dab(3,4-Dihydroxybenzoyl)-Gly—OH |
| 33 | Ac—Gly—Dab(3,4-Dihydroxyphenylacetyl)-Gly—OH |
| 34 | Ac—Gly—Lys(3,4-Dihydroxybenzoyl)-Gly—OH |
| 35 | Ac—Gly—Lys(3,4-Dihydroxyphenylacetyl)-Gly—OH |
| 36 | Ac—Glu—Orn(3,4-Dihydroxybenzoyl)-Gly—OH |
| 37 | Ac—Glu—Orn(3,4-Dihydroxyphenylacetyl)-Gly—OH |
| 38 | Ac—His—Orn(3,4-Dihydroxybenzoyl)-Gly—OH |
| 39 | Ac—His—Orn(3,4-Dihydroxyphenylacetyl)-Gly—OH |
| 40 | Ac—His—Dab(3,4-Dihydroxybenzoyl)-Gly—OH |
| 41 | Ac—His—Dab(3,4-Dihyroxyphenylacetyl)-Gly—OH |
| 42 | Ac—His—Lys(3,4-Dihydroxybenzoyl)-Gly—OH |
| 43 | Ac—His—Lys(3,4-Dihydroxyphenylacetyl)-Gly—OH |

A variety of analytical and spectroscopic methods were used to confirm the structure of the peptides prepared thus. Some results are compiled in Table 3.

TABLE 3

| Example No. | MS (FAB) | TLC ($R_f$) | $^1$H—NMR (a) | Others |
|---|---|---|---|---|
| 20 | 449 (M + 1) | 0.65 (Syst. 2) | + | AA |
| 21 | 449 (M + 1) | 0.48 (Syst. 2) | + | AA |
| 22 | 465 (M + 1) | 0.45 (Syst. 3) | + | |
| 23 | 481 (M + 1) | 0.31 (Syst. 3) | + | |
| 24 | 479 (M + 1) | 0.40 (Syst. 3) | + | |
| 25 | 479 (M + 1) | 0.42 (Syst. 3) | + | |
| 26 | 451 (M + 1) | 0.21 (Syst. 3) | + | |
| 27 | 465 (M + 1) | 0.30 (Syst. 3) | + | AA |
| 28 | 479 (M + 1) | 0.24 (Syst. 2) | + | |
| 29 | 493 (M + 1) | 0.25 (Syst. 2) | + | C,H,N-Analysis |
| 30 | 425 (M + 1) | 0.40 (Syst. 3) | + | |
| 31 | 439 (M + 1) | 0.38 (Syst. 3) | + | |
| 32 | 411 (M + 1) | 0.28 (Syst. 3) | + | |
| 33 | 425 (M + 1) | 0.30 (Syst. 3) | + | |
| 34 | 439 (M + 1) | 0.15 (Syst. 4) | + | |
| 35 | 453 (M + 1) | 0.25 (Syst. 4) | + | |
| 36 | 497 (M + 1) | 0.19 (Syst. 3) | + | C,H,N-Analysis |
| 37 | 511 (M + 1) | 0.25 (Syst. 3) | + | |
| 38 | 505 (M + 1) | 0.20 (Syst. 2) | + | |
| 39 | 519 (M + 1) | 0.24 (Syst. 2) | + | |
| 40 | 491 (M + 1) | 0.16 (Syst. 2) | + | |
| 41 | 505 (M + 1) | 0.16 (Syst. 2) | + | |
| 42 | 519 (M + 1) | 0.30 (Syst. 2) | + | |
| 43 | 533 (M + 1) | 0.31 (Syst. 2) | + | |

(a) measured at 60 or 270 MHz;
"+" means: consistent with the indicated structure

We claim:
1. A compound of the formula I

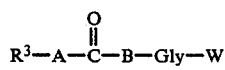

in which $R^3$ denotes ($C_1$-$C_8$)-alkyl which is optionally monosubstituted by carboxyl, amino, hydroxyl or ($C_1$-$C_4$)-alkoxy; ($C_3$-$C_8$)-cycloalkyl; ($C_3$-$C_8$)-cycloalkyl-($C_1$-$C_5$)-alkyl; ($C_6$-$C_{10}$)-aryl or ($C_6$-$C_{10}$)-aryl-($C_1$-$C_5$)-alkyl, both of which can optionally be substituted in the aryl moiety by one or two, identical or different, radicals from the series comprising carboxyl, amino, hydroxyl, ($C_1$-$C_4$)-alkoxy or halogen; ($C_3$-$C_9$)-heteroaryl or ($C_3$-$C_6$)-heteroaryl-($C_1$-$C_5$)-alkyl;

A represents —O—, —NH— or a direct bond;
B denotes a radical of the formula IIIa or IIIb;

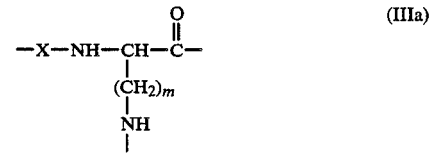

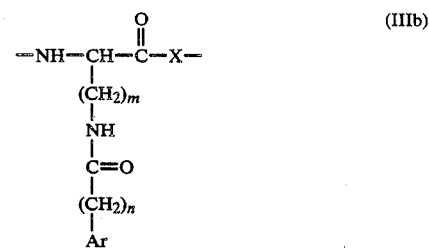

in which
X represents a radical of proline or 4-thiaproline or a radical of the formula IV

in which
$R^4$ denotes hydrogen or ($C_1$-$C_4$)-alkyl which is optionally monosubstituted by hydroxyl, carboxyl, carbamoyl, methylthio, phenyl, 4-hydroxyphenyl, 4-imidazolyl or 3-indolyl;
m represents 2, 3 or 4,
n represents 0 or 1, and
Ar represents mono-, di- or trihydroxyphenyl, and
W denotes hydroxyl or a radical of the formula V

in which
$R^1$ denotes hydrogen, ($C^1$-$C^6$)-alkyl or ($C^3$-$C^6$)-cycloalkyl, and
$R^2$ denotes hydrogen, ($C_1$-$C_6$)-alkyl or ($C_3$-$C_6$)-cycloalkyl, or
$R^1$ and $R^2$ together represent —[CH$_2$]$_4$— or —[CH$_2$]$_5$—, it being possible for one [CH$_2$]group to be replaced by —O— or —S—,
and its physiologically tolerated salts.

2. A compound as claimed in claim 1, in which X denotes a radical of proline or 4-thiaproline or a radical of the formula IV in which $R^4$ represents hydrogen, methyl, hydroxymethyl, 1-hydroxyethyl, isopropyl, isobutyl, sec.-butyl, carboxymethyl, 2-carboxyethyl, carbamoylmethyl, 2-carbamoylethyl, 2-methylthioethyl, phenylmethyl, (4-hydroxyphenyl)-methyl, 4-imidazolylmethyl or 3-indolylmethyl.

3. A compound as claimed in claim 1, in which X represents Gly, Pro, 4-Thia-Pro, His, Glu or Leu.

4. A compound as claimed in claim 1, in which $R^3$ represents optionally substituted $(C_1-C_8)$-alkyl, cyclopropyl, cyclobutyl, cyclopentyl, cyclohexyl, cyclopropylmethyl, cyclobutylmethyl, cyclopentylmethyl, cyclohexylmethyl, optionally substituted phenyl, optionally substituted benzyl, optionally substituted phenethyl, a heteroaryl radical from the series comprising 2-, 3- or 4-pyridyl, 2- or 3-pyrrolyl, 2- or 3-furyl, 2- or 3-thienyl, 4-imidazolyl or 1-, 3- or 4-isoquinolyl or such a heteroaryl radical which is bonded via —$CH_2$— or —$CH_2$—$CH_2$—.

5. A compound as claimed in claim 1, in which $R^3$ represents $(C_1-C_8)$-alkyl, $(C_1-C_8)$-alkyl which is monosubstituted by amino, hydroxyl, carboxyl, methoxy or ethoxy, or represents cyclopentyl, cyclohexyl, phenyl or mono- or dihalogenophenyl.

6. A compound as claimed in claim 1, in which a hydroxyl group is present in position 2 and/or 3 of the radical Ar.

7. A compound as claimed in claim 1, in which Ar represents 2-hydroxyphenyl, 3-hydroxyphenyl, 4-hydroxyphenyl, 2,3-dihydroxyphenyl, 3,4-dihydroxyphenyl or 3,4,5-trihydroxyphenyl.

8. A compound as claimed in claim 1, in which W represents hydroxyl, amino, $(C_1-C_6)$-alkylamino, cyclohexylamino, dimethylamino, diethylamino, ethylmethylamino, 1-piperidyl or 1-pyrrolidyl.

9. A pharmaceutical composition for inhibiting hydroxylating enzymes comprising an effective amount of a compound as claimed in claim 1 and a physiologically acceptable vehicle.

10. A method for inhibiting hydroxylating enzymes, which comprises use of an effective amount of a compound as claimed in claim 1 and a physiologically acceptable vehicle.

11. A method for inhibiting collagen biosynthesis, which comprises use of an effective amount of a compound as claimed in claim 1 and a physiologically acceptable vehicle.

* * * * *